US007910840B2

(12) United States Patent
Chai

(10) Patent No.: US 7,910,840 B2
(45) Date of Patent: Mar. 22, 2011

(54) APPARATUS AND METHOD FOR DETERMINING GROWTH STATUS OF A HUMAN SUBJECT

(75) Inventor: John Y. Chai, Hong Kong (HK)

(73) Assignee: Fook Tin Technologies Ltd., Hong Kong (HK)

( * ) Notice: Subject to any disclaimer, the term of this patent is extended or adjusted under 35 U.S.C. 154(b) by 0 days.

(21) Appl. No.: 11/827,076

(22) Filed: Jul. 10, 2007

(65) Prior Publication Data

US 2008/0179110 A1 Jul. 31, 2008

(51) Int. Cl.
*G01G 9/00* (2006.01)
(52) U.S. Cl. .................... 177/25.16; 177/25.19; 128/921
(58) Field of Classification Search ............... 177/25.16, 177/25.19, 245; 33/512; 128/921; 702/173
See application file for complete search history.

(56) References Cited

U.S. PATENT DOCUMENTS

| 3,655,003 | A | | 4/1972 | Yamajima |
| 3,808,694 | A | * | 5/1974 | Hutchinson et al. ............ 33/512 |
| 3,866,699 | A | | 2/1975 | Soehnle et al. |
| 3,895,356 | A | * | 7/1975 | Kraus ........................... 702/161 |
| 3,967,690 | A | | 7/1976 | Northcutt |
| 4,113,039 | A | | 9/1978 | Ozaki et al. |
| 4,844,187 | A | * | 7/1989 | Jabero ............................. 177/5 |
| 5,449,000 | A | | 9/1995 | Libke et al. |
| 5,763,837 | A | * | 6/1998 | Davignon et al. ......... 174/113 R |
| 6,354,996 | B1 | | 3/2002 | Drinan et al. |
| 6,369,338 | B1 | * | 4/2002 | Kimura ...................... 177/25.16 |
| 6,538,215 | B2 | * | 3/2003 | Montagnino et al. ...... 177/25.16 |
| 6,539,310 | B2 | | 3/2003 | Shimomura |
| 6,853,949 | B2 | * | 2/2005 | Honda ........................... 702/173 |
| 6,865,415 | B2 | | 3/2005 | Kawanishi |
| 6,969,350 | B1 | | 11/2005 | Hawthorne et al. |
| 7,170,016 | B2 | * | 1/2007 | Dumornay et al. ......... 177/25.13 |
| 7,200,952 | B2 | * | 4/2007 | Montagnino .................... 33/832 |
| 2002/0049546 | A1 | | 4/2002 | Shimomura |
| 2002/0111559 | A1 | | 8/2002 | Kurata et al. |

(Continued)

FOREIGN PATENT DOCUMENTS

CA  2133156  3/1996

(Continued)

OTHER PUBLICATIONS

W-Y Lin, et al., Optimal Cut-Off Values for Obesity. International Journal of Obesity, 2002, 26: 1232-38, Taiwan.

(Continued)

*Primary Examiner* — Randy W Gibson
(74) *Attorney, Agent, or Firm* — Stroock & Stroock & Lavan LLP

(57) ABSTRACT

A measurement device and method that in one aspect determines and displays percentile information relating to growth indices, such as BMI, weight-for-length, and weight-for-height, based on a subject's age and gender. The device and method may also provide classification information, such as whether the percentile information is considered to be, for example, below normal, normal, above normal, or far above normal. The device and method may additionally indicate, for example, the normal range of the subject's weight based on the subject's height, the subject's height based on the subject's weight and the normal range of BMI based on the subject's age and gender. In still another aspect, the device and method may indicate predictive values of the subject's future weight, height, BMI or head circumference based on the subject's present measurement values and growth percentiles.

30 Claims, 6 Drawing Sheets

U.S. PATENT DOCUMENTS

| | | | |
|---|---|---|---|
| 2006/0122470 | A1 | 6/2006 | Schulz |
| 2007/0068539 | A1 | 3/2007 | Hall et al. |
| 2008/0183421 | A1* | 7/2008 | Chai .............................. 702/173 |
| 2008/0294370 | A1* | 11/2008 | Kriger ........................... 702/173 |

FOREIGN PATENT DOCUMENTS

| | | |
|---|---|---|
| JP | 2001-091346 | 4/2001 |
| JP | 2002-165764 | 6/2002 |
| WO | WO 98/13674 | 4/1998 |
| WO | WO 2005/043443 | 5/2005 |
| WO | WO 2007/040971 | 4/2007 |

OTHER PUBLICATIONS

Dr. Margaret Ashwell Obe, The Ashwell Shape Chart. Ashwell Associates, United Kingdom.

OMRON Healthcare, Inc., Omron Instruction Manual for Body Composition Monitor with Scale Model HBF-500, 2006, China.

Tanita Corporation, InnerScan Body Composition Monitor Guide Model BC-533, 2005.

Scott M. Grundy, et al., Definition of Metabolic Syndrome. Circulation, Journal of the American Heart Association, 2004, 109: 433-438, American Heart Association, USA.

Earl S. Ford, MD, MPH, et al., Prevalence of the Metabolic Syndrome Among US Adults, JAMA, 2002, vol. 287, No. 3, 2002, American Medical Association, USA.

MEJ Lean, Waist Circumference as a Measure for Indicating Need for Weight Management (abstract), BMJ, 1995, 311: 158-161, BMJ Publishing Group, United Kingdom.

Dr. Margaret Ashwell, et al., Ratio of Waist Circumference to Height May Be Better Indicator of Need for Weight Management, BMJ, 1996, 312:377, BMJ Publishing Group, UK.

Shiun Dong Hsieh, MD, et al., The Superiority of Waist-to-Height Ratio . . . , Preventive Medicine, 2004, 40: 216-220, Institute for Cancer Prevention and Elsevier Inc.

G. Valsamakis, et al., Association of Simple Anthropometric Measures of Obesity with Visceral Fat . . . , Diabetic Medicine, 2004, 21: 1339-1345, Diabetes UK, UK.

Database Biosis (Online) Biosciences Information Service, Philadelphia, PA, US; 1996, Ashwell M A et al: "Use of the waist:height ration to assess the risks of obesity" XP002479620 Database accession No. PREV199699127163*the whole document* & Proceedings of the Nutrition Society, vol. 55, No. 1, 1996, p. 83A, Scientific Meeting of the Nutrition Society; Aberdeen, Scotland, UK; Jul. 10-14, 1995 ISSN: 0029-6651.

National Heart, Lung and Blood Institute, Information for Patients and the Public, Assessing your Risk, www.nhibi.nih.gov/health/public/heart/obesity/lose_wt/bmi_dis.htm.

National Heart, Lung and Blood Institute, Information for Patients and the Public, Classification of Over . . . , www.nhibi.nih.gov/health/public/heart/obesity/lose_wt/bmi_dis.htm.

Omron Healthcare, Inc., Omron Body Composition Scale "Karada Scan" Series, model HBF-355, p. 1 and 16.

Expert Panel . . . , Clinical Guidelines on the Identification, Evaluation and Treatment . . . , The AM Journal of Clinical Nutrition, 1998; 68:899-917, Am. Soc. of Clinical Nut.

Tseng, Pathophysiology/Complications: Waist-to-Height Ratio Is Independently and Better Associated with Urinary Albumin Excretion Rate Than Waist Circumference or Waist-to-Hip Ratio in Chinese Adult Type 2 Diabetic Woman, but Not Men, Sep. 2005, Diabeties Care, vol. 28, No. 9, pp. 2249-2251.

Cunningham et al., "Overweight and Obesity Indigenous Austrialians", May 1998, Australian Bureau of Statistics, pp. 1-58.

* cited by examiner

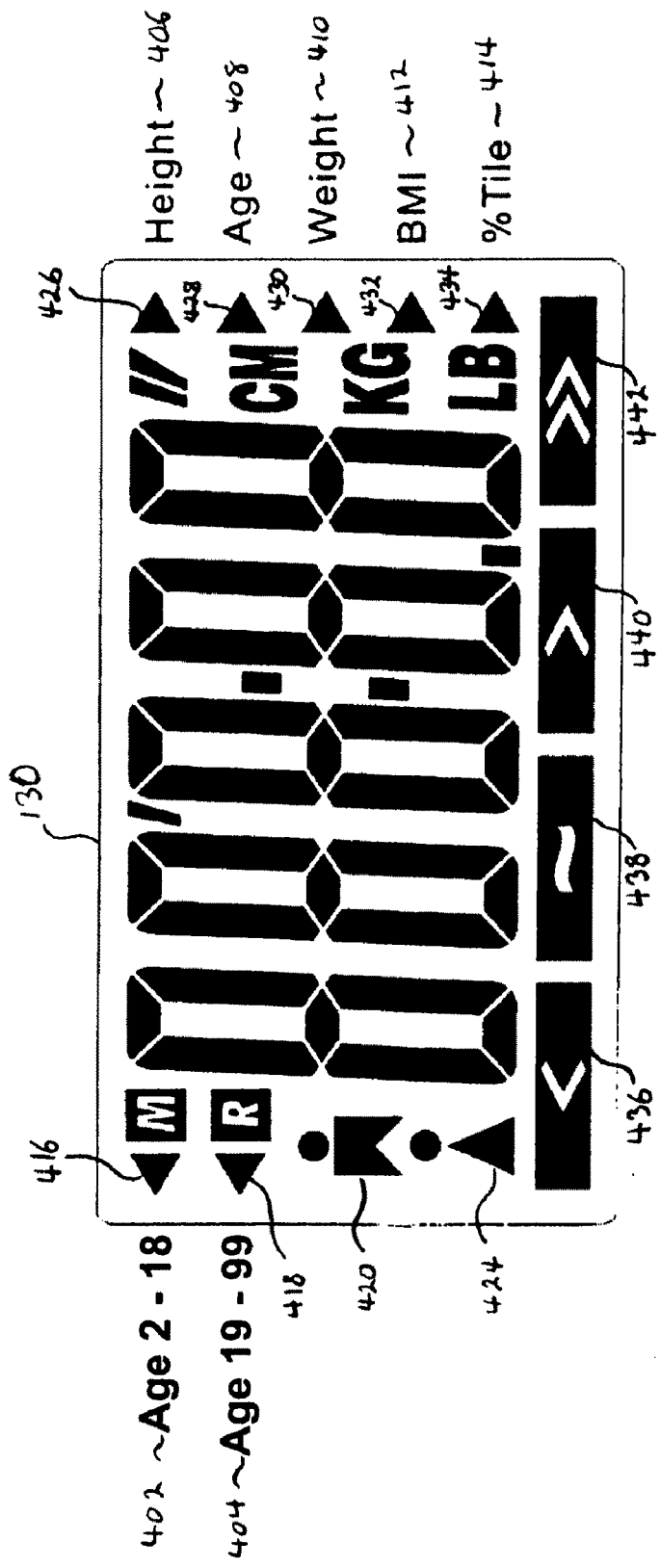

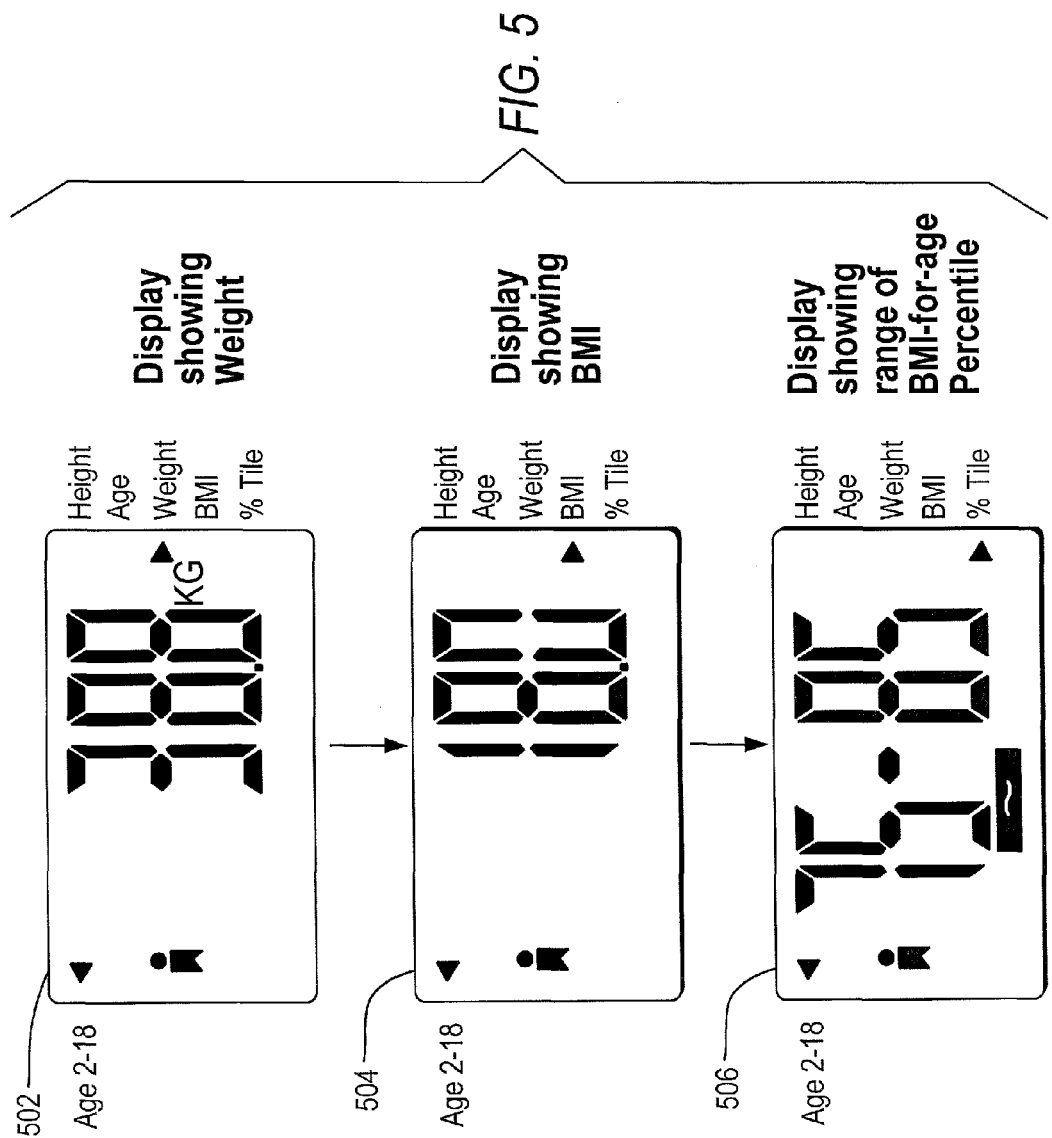

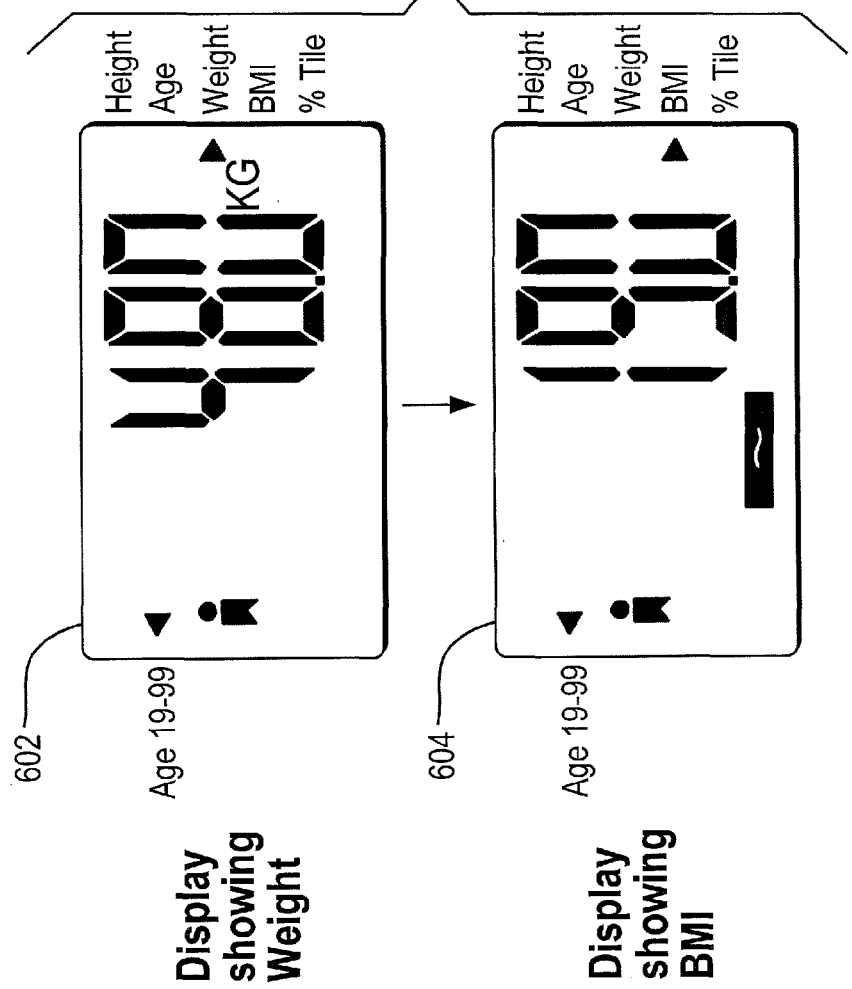

APPARATUS AND METHOD FOR DETERMINING GROWTH STATUS OF A HUMAN SUBJECT

BACKGROUND OF THE INVENTION

Anthropometric measurements such as height, weight, body length and head circumference have been used by medical professionals as parameters to monitor the growth of a baby, child or adolescent. Such parameters vary according to the age of the subject. Through population studies, population percentiles of such parameters have been established. It is common practice for pediatricians to measure those parameters for their patients and plot the results on respective growth charts so that the growth status of a child for each of the parameters can be determined. The apparatuses used to measure such parameters include tape measures, standing stadiometers and weighing scales.

Davignon described in CA 2,133,156A and U.S. Pat. No. 5,763,837 how to improve the recording of weight and height, and estimating weight and height growth percentiles. Through the use of a weight and height measurement system, the measured weight and height of the subject is compared to growth height and weight tables relative to the sex and age category of the subject. The system then calculates the percentile weight and height of the subject from these tables.

It is also known from the medical literature that the weight and height of a child is not, by themselves, as indicative of the subject's growth pattern as certain growth indices. Examples of such growth indices are Body Mass Index (BMI) for children and adolescents, which is represented as body mass (kg) divided by the square of body height ($m^2$), weight-for-length for infants, and weight-for-height for preschoolers. While current weight scales and weight/height measurement devices provide BMI results or the results of other indices (WO 98/13674, US 2002/00049546A1, JP2002-165764, JP2001-091346), they do not, to the inventor's knowledge, determine and display percentile information relating to growth indices based on the subject's age and gender. They also do not characterize that information in terms of whether it is considered to be, for example, below normal, normal, above normal, or far above normal.

There is accordingly a need for a measurement device that determines and displays percentile information relating to growth indices, such as BMI, weight-for-length, and weight-for-height, based on the subject's age and gender. There is also a need for a measurement device that readily provides classification information, such as whether the percentile information is considered to below normal, normal, above normal, or far above normal.

SUMMARY OF THE INVENTION

The present invention provides a measurement device that determines and displays percentile information relating to growth indices, such as BMI, weight-for-length, and weight-for-height, based on a subject's age and gender.

In another aspect, the present invention provides classification information, such as whether the percentile information is considered to be, for example, below normal, normal, above normal, or far above normal. For example, in one embodiment, a measurement device in accordance with the present invention may indicate whether the BMI-for-age percentile, for ages 2-18, is in one of the following four ranges: underweight, normal, risk of overweight, and overweight.

To assist the subject in understanding his or her normal growth profile, another embodiment of the measurement device may additionally indicate, for example, the normal range of the subject's weight based on the subject's height, the subject's height based on the subject's weight and the normal range of BMI based on the subject's age and gender.

In yet another embodiment, the measurement device may also indicate predictive values of the subject's future weight, height, BMI or head circumference based on the subject's present measurement values and growth percentiles. Such an embodiment helps the subject in understanding his or her growth trend.

BRIEF DESCRIPTION OF THE DRAWINGS

Additional objects and features of the invention will be more readily apparent from the following detailed description and appended claims when taken in conjunction with the drawings, in which:

FIG. 4 depicts an exemplary LCD display in accordance with the present invention.

FIG. 5 shows a sequence of display screens during measurement of a male child or adolescent.

FIG. 6 shows a sequence of display screens during measurement of an adult male.

Like reference numerals refer to corresponding parts throughout the several views of the drawings.

DETAILED DESCRIPTION OF THE PREFERRED EMBODIMENTS

Figure 1:
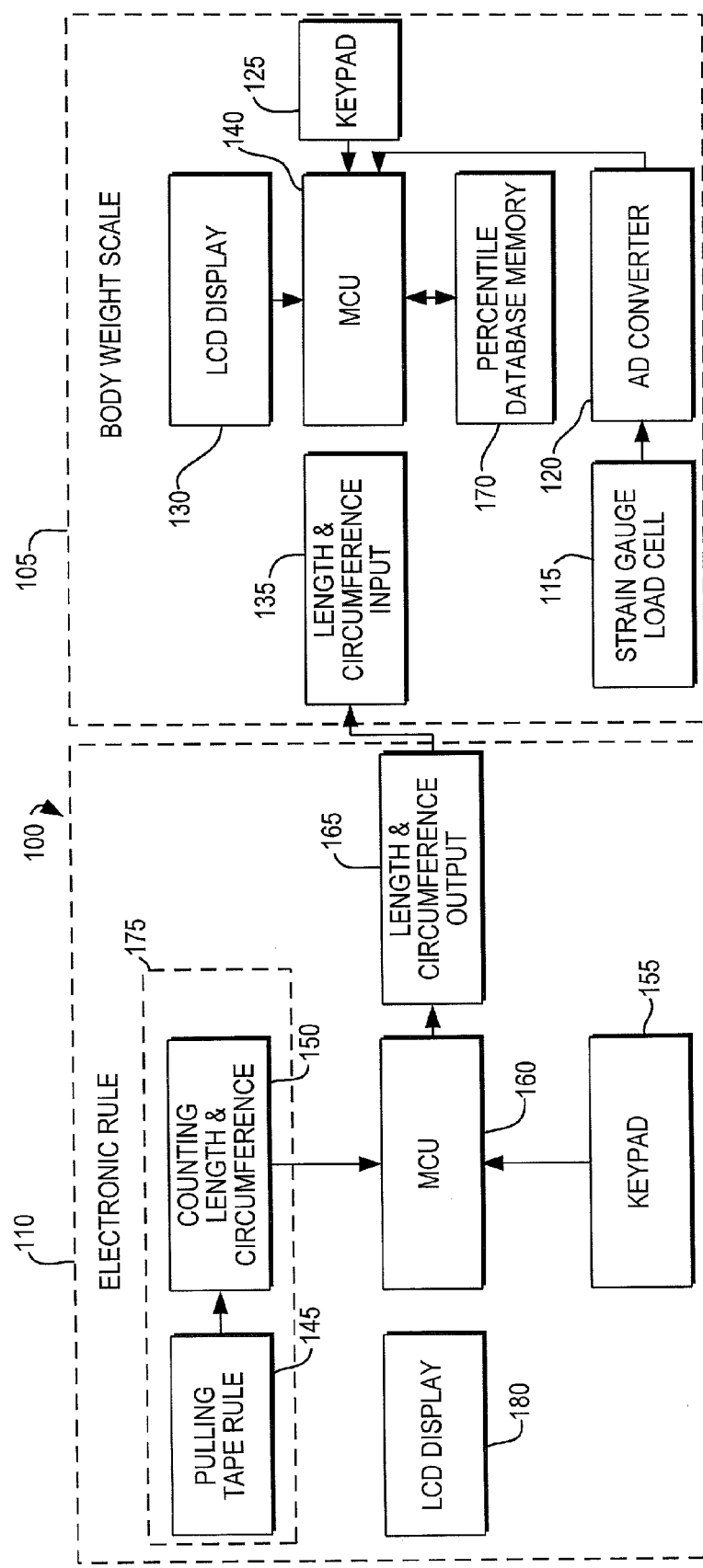
FIG. 1 is a block diagram of a measurement device in accordance with the present invention.

FIG. 1 is a block diagram of a measurement device 100 in accordance with the present invention. Device 100 includes a body weight scale 105 and an optional electronic rule 110.

Body weight scale 105 includes strain gauge load cell 115, A/D converter 120, keypad 125, LCD display 130, optional length & circumference input 135, micro control unit (MCU) 140, and percentile database memory 170. Strain gauge load cell 115 produces an analog signal corresponding to and indicative of the weight of a subject positioned on it, as is well known in the art. That analog signal is converted into a digital signal by A/D converter 120 and then input to MCU 140. Alternatively, instead of strain gauge load cell 115 and/or A/D converter 120, any suitable weight measurement system that produces a digital signal corresponding to the weight of a subject may be used. MCU 140 can be any type of digital device capable of performing the operations described below of a measurement device in accordance with the present invention, including, but not limited to, a microcontroller, microprocessor, programmable logic array, or application specific integrated circuit (ASIC). Keypad 125 is used to enter additional information into MCU 140, such as the subject's age, sex, and, optionally, length/height and, in certain embodiments, head circumference. Alternatively, length/height and/or head circumference information may be entered through length & circumference input 135, which in turn may receive that information from electronic rule 110, described below. LCD display 130 displays various information input into or determined by MCU 140. Percentile database memory 170 contains percentile information for various growth indices based on age and gender. It may also contain other information that may be used in embodiments of the present invention. Various electronic components of body weight scale 105 are powered by a battery or other power supply, not shown.

Electronic rule 110, if present, may be any device that electronically measures a subject's length or height and/or the circumference of a subject's head. Such devices are well known in the art. In one embodiment, electronic rule 110 includes tape rule or height measurement device 175, MCU 160, keypad 155, LCD display 180 and length and circumference output 165.

Tape rule or height measurement device 175 may be any suitable device known in the art for electronically determining the length or height of a subject or the circumference of a subject's head. It may include, for example, a pulling tape or rod rule 145 and a counting length and circumference unit 150. Pulling tape or rod rule 145 may comprise a reel of soft tape or a height rod having holes distributed at known intervals along its length through which light emitted from an LED may pass. Counting length and circumference unit 150 detects and counts the pulses as the tape or rod is advanced with increasing length or height and uses the count to determine the measured length/height of the subject and/or the circumference of a part of the subject's body, such as the head. The length/height information and/or circumference is input into MCU 160, which in turn sends it, via length and circumference output 165, to the length and circumference input 135 of body weight scale 105. Various electronic components of electronic rule 110 are likewise powered by a battery or other power supply, not shown.

Figure 2:
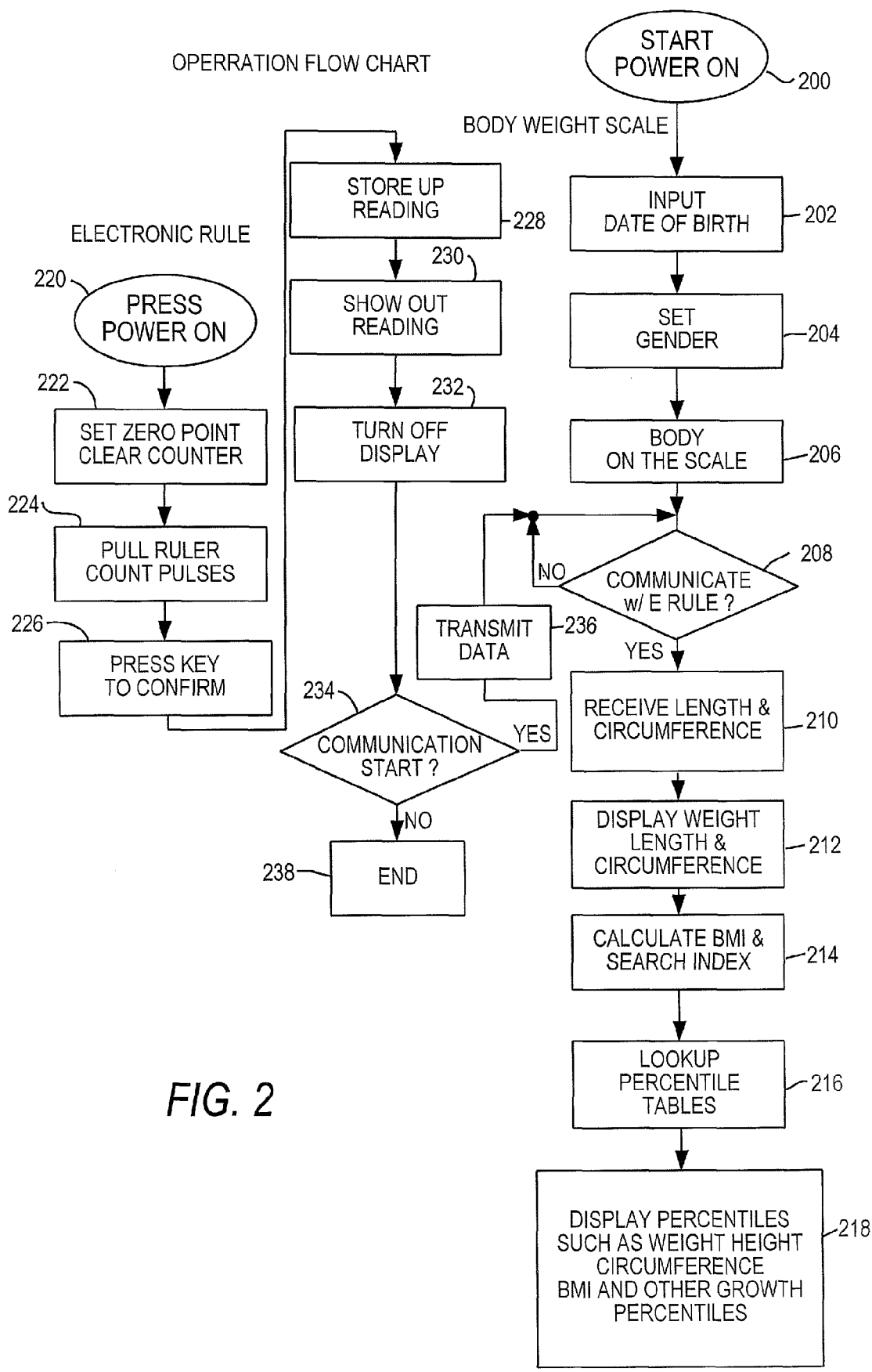
FIG. 2 is a flow chart illustrating the operation of a measurement device in accordance with the present invention.

FIG. 2 is a flow chart illustrating the operation of a measurement device in accordance with the present invention. Steps 200 through 218 relate to the operation of body weight scale 105. Steps 220 through 238 relate to the operation of electronic rule 110, if present.

In step 200, body weight scale 105 is powered on. In step 202, the subject's date of birth is entered into MCU 140 and, in step 204, the subject's gender is entered into MCU 140, both via keypad 128. In step 206, the subject is weighed on strain gauge load cell 115, causing the subject's weight to be entered into MCU 140 via A/D converter 120. Alternatively, instead of strain gauge load cell 115 and A/D converter 120, other suitable weight measuring components or devices may be used that are capable of generating a digital signal corresponding to a subject's weight. In step 208, MCU 140 attempts to communicate with electronic rule 110, and, if successful, receives length and/or height and, optionally, circumference information in step 210. Alternatively, steps 208 and 210 can be eliminated and the length/height and/or circumference information can instead be entered into MCU 140 via keypad 125. In step 212, the weight, length/height and/or optional circumference information may be displayed on display 130.

In step 214, MCU 140 calculates the subject's BMI, or other growth index. BMI is equal to weight (kg)÷(stature (cm))$^2$×10,000 or weight (lb)÷(stature (in))$^2$×703. In step 216, MCU 140 then retrieves corresponding percentile information, including BMI or other growth index percentile information, from percentile database memory 170, based on the BMI, or other growth index, and the subject's age and gender. MCU 140 may also retrieve corresponding percentile information for the subject's weight, height and/or circumference, or other growth percentiles. Alternatively, percentile information can also be derived from formulas, where known in the art. In step 218, the percentile information, including the BMI or other growth index percentile, and weight, height, circumference, and/or other growth percentiles may be displayed on display 130. In addition, classification information indicating whether the displayed measurement, index, or percentile information is considered to below normal, normal, above normal, or far above normal, may also be displayed.

In embodiments equipped with a "normal range" function, the range of normal values for a given growth measurement, based on the subject's age, gender and/or other growth measurements, may also be displayed. For example, the normal range value of height, weight, head circumference or BMI of a 5-year-old male child may be displayed. Similarly, the normal range value of weight for a given length or height of an infant or child may be displayed.

In embodiments including the growth trend feature, MCU 140 may retrieve from percentile database memory 170 growth values and indices, such as height, weight, head circumference or BMI corresponding to the subject's future age based on the subject's present percentile. For example, given the height of a 12-year-old male subject's fits into the 50th percentile of the population, MCU 140 retrieves the 50th percentile height value of a male subject at, for example, 17 years old and displays such a predictive value on display 130.

In embodiments including electronic rule 110, in step 220, electronic rule 110 is powered on. In step 222, electronic rule 110 is cleared to zero if necessary. In step 224, tape rule 145 is pulled and the resulting pulses are counted by counting length and circumference unit 150. In step 226, when the desired length is reached, a key is pressed to confirm that measurement is complete. In step 228, the measurement is then stored in MCU 160 and, in step 230, displayed on LCD display 180, if present. If display 180 is not present, the measurement may be displayed on LCD display 130, in which case a suitable connection must be provided between MCU 160 and LCD display 130. In step 232, the display is turned off after a predetermined period of time.

In step 234, MCU 160 in electronic rule 110 waits for a communication request from MCU 140 in body weight scale 105. If a communication request is received, MCU 160 transmits, in step 236, the measurement information, via length and circumference output 165, to the length and circumference input 135 in body weight scale 105. If no communication request is received or a communication is otherwise not initiated, the process ends in step 238.

For Caucasian adults, a BMI over 30 is considered obese; between 25 and 29.9 is considered overweight, between 18.5 and 24.9 is considered normal (a healthy BMI); and under 18.5 is considered underweight. These ranges may differ for different races.

For children and adolescents, ages 2 to 18, body fatness changes with age and is gender dependent. A BMI in the $95^{th}$ percentile or greater is considered overweight; in the $85^{th}$ to $95^{th}$ percentile is considered at risk of being overweight; in the $5^{th}$ to $85^{th}$ percentile is considered to be normal; and less than the $5^{th}$ percentile is considered to be underweight.

The percentile information that is stored in percentile database memory is publicly available from, for example, the National Center for Health Statistics (which is part of the U.S. Department Of Health And Human Services' Centers for Disease Control and Prevention).

An exemplary embodiment of a measurement device in accordance with the present invention includes: high precision strain gauge technology for weight measurement; a weighing function; BMI calculation; BMI-for-age Percentile, which displays percentile for children and adolescents (2-18 years of age) according to age and gender; Classification of BMI-for-age Percentile (2-18 years of age) according to four categories: underweight, normal, risk of overweight and overweight; Classification of BMI for adults according to four categories: underweight, normal, overweight and obese;

3-button operation; 4-user memories for input data (age, gender, and, optionally, height), which stores information for four users; fast recall function; memory clear function, which clears some or all of the information in the user memories; auto-on and auto-off function, which automatically turn the measurement device on when the subject is placed on the weighing scale and off a few seconds after the subject is removed from the weighing scale in order to save power; power saving LCD readout; low-battery indicator; 150 kg or 330 lb weight capacity; 100 g or 0.2 lb graduation; age range from 2 to 99 years; height range from 100 cm to 220 cm (3'3.4" to 7'2.6"); and two CR2032 lithium batteries.

Figure 3:
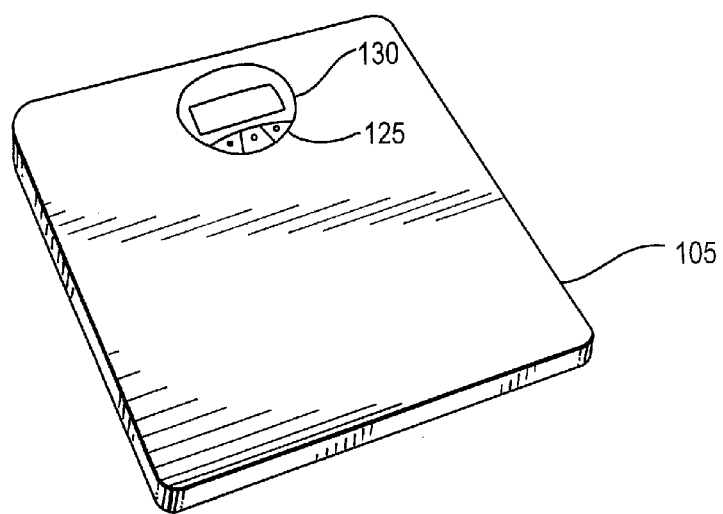
FIG. 3 is an example of a body weight scale in accordance with the present invention.

An example of a body weight scale 105, having a 3-button keypad 125 and an LCD display 130 is shown in FIG. 3.

FIG. 4 depicts an exemplary LCD display 130 in which all display segments are illuminated for explanatory purposes. Indicia 402, 404, 406, 408, 410, 412, and 414 are printed on the surface adjacent to display 130. Indicator 416 is illuminated if the age of the subject, as determined by the entered birthdate, is between 2 and 18. Indicator 418 is illuminated if the age of the subject is between 19 and 99. Indicator 420 is illuminated if the subject is male and indicator 424 is illuminated if the subject is female, again as determined from the entered gender information. Indicator 426 is illuminated if the height is currently being displayed; indicator 428 is illuminated if the age is currently being displayed; indicator 430 is illuminated if the weight is currently being displayed; indicator 432 is illuminated if the BMI is currently being displayed; and indicator 434 is illuminated if the BMI percentile is currently being displayed. Indicator 436 is illuminated if the subject's BMI percentile indicates that the subject is underweight; indicator 438 is illuminated if the subject's BMI percentile indicates that the subject is normal; indicator 440 is illuminated if the subject's BMI percentile indicates that the subject is overweight (for adults) or at risk of becoming overweight (for children and adolescents); and indicator 442 is illuminated if the subject's BMI percentile indicates that the subject is obese (for adults) or overweight (for children and adolescents). Indicators 436, 438, 440 and 442 more generally indicate whether the value being displayed is considered to be below normal, normal, above normal, or far above normal. For example, in certain embodiments, head circumference-for-age, height-for-age, and/or weight-for-age percentiles may be displayed, in which case indicators 436, 438, 440 and 442 would indicate whether those values are below normal, normal, above normal, or far above normal. Similarly, weight-for-length, and/or weight-for-height percentiles may be displayed in which case indicators 436, 438, 440 and 442 would likewise indicate the classification of those percentiles. Other portions of display 130 display the various values mentioned above, and other values, in appropriate units.

FIG. 5 shows a sequence of display screens during measurement of a male child or adolescent. Display screen 502 indicates that the subject is 38.8 kg. Display screen 504 indicates that the subject has a BMI of 18.0. Display screen 506 indicates that the subject has a BMI percentile of 75-85%. The illuminated indicator on the bottom of display screen 506 indicates that the subject's BMI percentile is in the normal range.

FIG. 6 shows a sequence of display screens during measurement of an adult male. Display screen 602 indicates that the subject is 48.0 kg. Display screen 604 indicates that the subject has a BMI of 19.0 and that that BMI is in the normal range.

The illustrative descriptions of the application of the principles of the present invention are to enable any person skilled in the art to make or use the disclosed invention. These descriptions are susceptible to numerous modifications and alternative arrangements by those skilled in the art. Such modifications and alternative arrangements are not intended to be outside the scope of the present invention. The appended claims are intended to cover such modifications and arrangements. Thus, the present invention should not be limited to the described illustrative embodiments but, instead, is to be accorded the broadest scope consistent with the principles and novel features disclosed herein.

The invention claimed is:

1. A device for providing growth status of a human subject comprising:
   one or more measurement systems that determine one or more anthropometric measurements;
   a micro control unit connected to the one or more measurement systems;
   a memory device connected to the micro control unit; and
   an input device connected to the micro control unit;
   wherein
   the memory device stores growth index percentile information based on age and gender; and
   the micro control unit is capable of determining a growth index percentile value based on two or more anthropometric parameters obtained from user information relating to the subject input on the input device or measurement information generated by the one or more measurement systems, and the growth index percentile information stored in the memory device.

2. The device of claim 1 wherein one of the measurement systems comprises a weight measurement system.

3. The device of claim 1 further comprising:
   a display connected to the micro control unit, wherein the display is capable of displaying information relating to the growth index percentile value.

4. The device of claim 2, wherein the weight measurement system comprises a load cell and an analog-to-digital converter.

5. The device of claim 1, wherein the growth index percentile information comprises body mass index for age percentile information.

6. The device of claim 1, wherein the micro control unit is further capable of determining which of a plurality of categories the given growth index percentile value falls.

7. The device of claim 6, wherein the plurality of categories include one or more of below normal, normal, above normal, or far above normal.

8. The device of claim 1, wherein the input device is a keypad.

9. The device of claim 1, wherein the user information includes one or more of age information, gender information, length or height information, or head circumference information.

10. The device of claim 1, wherein the growth index percentile information comprises one or more of weight-for-length or weight-for-height percentile information.

11. The device of claim 3 wherein
   the memory device further stores range information regarding one or more of a normal range of weight for a given age, length or height, a normal range of length or height for a given age or weight, or a normal range of head circumference or body mass index for a given age;
   the micro control unit is capable of determining normal range information corresponding to one or more of the user information input on the input device or measurement information generated by the one or more measurement systems; and the normal range information is displayed on the display device.

12. The device of claim 1 wherein
the memory device further stores one or more of length for age or head circumference for age percentile information; and
the micro control unit is capable of determining one or more of a length for age percentile value or a head circumference for age percentile value based on one or more of the user information input on the input device or the measurement information generated by the one or more measurement systems, and the length for age or head circumference for age percentile information stored in the memory device.

13. The device of claim 3 wherein
the memory device further stores, for each age in a range of ages, percentile information regarding one or more of weight, height, body mass index, or head circumference;
the micro control unit is capable of determining percentile information for one or more of weight, height, body mass index, or head circumference based on one or more of the user information input on the input device or measurement information generated by the one or more measurement systems, and determining a predictive value for one or more of weight, height, body mass index or head circumference based on a respective present value and a present age; and
the predictive value is displayed on the display device.

14. The device of claim 1 wherein one of the measurement systems comprises an electronic rule.

15. The device of claim 14 wherein the electronic rule comprises a pulling tape or rod rule and a counting length or circumference unit.

16. A method of providing growth status information of a human subject comprising:
receiving measurement information comprising one or more anthropometric measurements of the subject from one or more measurement systems;
receiving user information relating to the subject input from an input device; and
determining a growth index percentile value based on two or more anthropometric parameters obtained from the user information relating to the subject or the measurement information, and growth index percentile information for age and gender stored in a memory device.

17. The method of claim 16 wherein one of the measurement systems comprises a weight measurement system.

18. The method of claim 16 further comprising:
displaying information relating to the growth index percentile value.

19. The method of claim 17, wherein the weight measurement system comprises a load cell and an analog-to-digital converter.

20. The method of claim 16, wherein the growth index percentile information comprises body mass index for age percentile information.

21. The method of claim 16 further comprising determining which of a plurality of categories the given growth index percentile value falls.

22. The method of claim 21, wherein the plurality of categories include one or more of below normal, normal, above normal, or far above normal.

23. The method of claim 16, wherein the input device is a keypad.

24. The method of claim 16, wherein the user information includes one or more of age information, gender information, length or height information, or head circumference information.

25. The method of claim 16, wherein the growth index percentile information comprises one or more of weight-for-length or weight-for-height percentile information.

26. The method of claim 18 wherein the memory device further stores range information regarding one or more of a normal range of weight for a given age, length or height, a normal range of length or height for a given age or weight, or a normal range of head circumference or body mass index for a given age;
and further comprising
determining normal range information corresponding to one or more of the user information or the measurement information; and
displaying the normal range information.

27. The method of claim 16 wherein the memory device further stores one or more of length for age or head circumference for age percentile information;
and further comprising
determining one or more of a length for age percentile value or a head circumference for age percentile value based on one or more of the user information input on the input device or the measurement information generated by the one or more measurement systems, and the length for age or head circumference for age percentile information stored in the memory device.

28. The method of claim 18 wherein
the memory device further stores, for each age in a range of ages, percentile information regarding one or more of weight, height, body mass index, or head circumference;
and further comprising
determining percentile information for one or more of weight, height, body mass index, or head circumference based on one or more of the user information input or the measurement information,
determining a predictive value for one or more of weight, height, body mass index or head circumference based on a respective present value and a present age; and
displaying the predictive value.

29. The method of claim 16 wherein one of the measurement systems comprises an electronic rule.

30. The method of claim 29 wherein in the electronic rule comprises a pulling tape or rod rule and a counting length or circumference unit.

* * * * *